United States Patent [19]

Korb et al.

[11] Patent Number: 5,278,151

[45] Date of Patent: * Jan. 11, 1994

[54] DRY EYE TREATMENT SOLUTION

[75] Inventors: Donald R. Korb, Boston, Mass.; Thomas Glonek, Oak Park, Ill.; Jack Greiner, Winchester, Mass.

[73] Assignee: Ocular Research of Boston, Inc., Boston, Mass.

[*] Notice: The portion of the term of this patent subsequent to Dec. 28, 2010 has been disclaimed.

[21] Appl. No.: 898,380

[22] Filed: Jun. 9, 1992

Related U.S. Application Data

[63] Continuation of Ser. No. 529,657, May 29, 1990, abandoned, which is a continuation-in-part of Ser. No. 457,086, Dec. 26, 1989, abandoned, which is a continuation-in-part of Ser. No. 111,874, Oct. 23, 1987, Pat. No. 4,914,088, which is a continuation-in-part of Ser. No. 33,185, Apr. 2, 1987, abandoned.

[51] Int. Cl.$^5$ .............................................. A61K 31/685
[52] U.S. Cl. ...................................... 514/76; 514/912
[58] Field of Search ............................ 514/75, 76, 912

[56] References Cited

U.S. PATENT DOCUMENTS

| | | | |
|---|---|---|---|
| 4,421,748 | 6/1985 | Trager et al. | 514/78 |
| 4,522,803 | 6/1985 | Lenk et al. | 424/121 |
| 4,677,099 | 6/1987 | Shinitzky et al. | 514/78 |
| 4,804,539 | 2/1989 | Guo et al. | 424/450 |
| 4,818,537 | 4/1989 | Guo | 424/427 |
| 4,839,175 | 6/1989 | Guo et al. | 424/450 |
| 4,866,049 | 9/1989 | Maumenee et al. | 514/169 |
| 4,908,154 | 3/1990 | Cook et al. | 252/314 |
| 4,938,965 | 7/1990 | Shek et al. | 514/78 |

FOREIGN PATENT DOCUMENTS

| | | |
|---|---|---|
| 16149 | 1/1978 | Australia . |
| 0241376 | 10/1987 | European Pat. Off. . |
| 0312814 | 4/1989 | European Pat. Off. . |
| 0391369 | 4/1990 | European Pat. Off. . |
| 1-146824 | 6/1989 | Japan . |

OTHER PUBLICATIONS

Hardberger, Hana and Boyd, "Effects of Drug Vehicles on Ocular Contact Time," Arch Opthalmol., vol. 93, Jan. 1975.

F. Holly, *Contacto*, 26(5), pp. 9-13 (Sep. 1982).

Federal Register, 7076-7093 (Mar. 4, 1988).

*Primary Examiner*—Frederick E. Waddell
*Assistant Examiner*—Zohreh A. Fay
*Attorney, Agent, or Firm*—Robert L. Goldberg; Peter F. Corless

[57] ABSTRACT

A method and composition for reducing evaporation of an aqueous layer from the surface of the eye. The method comprises applying an admixture of a charged phospholipid and a non-polar oil over the eye, preferably in the form of a finely divided oil in water emulsion.

45 Claims, No Drawings

DRY EYE TREATMENT SOLUTION

CROSS REFERENCE TO RELATED APPLICATIONS

This is a continuation of copending application(s). Ser. No. 07/529,657 filed on May 29, 1990, now abandoned, which is a continuation in part of copending U.S. patent application Ser. No. 07/457,086 filed Dec. 26, 1989 now at which latter application is a continuation in part of U.S. patent application Ser. No. 07/111,874 filed Oct. 23, 1987, now U.S. Pat. No. 4,914,088, which in turn is a continuation in part of U.S. patent application Ser. No. 07/033,185 filed Apr. 2, 1987, now abandoned.

BACKGROUND OF THE INVENTION

1. Introduction

This invention relates to a means for wetting the surface of the eye, providing mechanical lubrication to the eye and reducing the evaporation of fluid from the surface of the eye. This invention also relates to a means for delivering a medicament to the corneal surface. More particularly, the invention relates to a composition capable of augmenting and maintaining a stable tear film over the corneal surface and/or to delivering a medicament to said surface. In a preferred embodiment of the invention, the invention relates to an ophthalmic composition for dry eye treatment.

2. Description of the Prior Art

It is known in the art that an aqueous tear film extends over the corneal surface which functions to maintain the corneal surface moist and lubricated. It is also known in the art that dehydration of moisture from the eye can result in discomfort, and compositions are available in the market intended to prevent evaporation from the tear film. These compositions are primarily aqueous film forming materials that provide a barrier layer that inhibits the evaporation of moisture.

The feeling of discomfort resulting from a dry eye condition includes ocular dryness, grittiness, burning, soreness or scratching dependent upon the subject and his condition. Proposed causes for dry eye, treatment and symptoms are all described in a compendium of papers on this subject edited by Holly, *The Preocular Tear Film in Health, Disease, and Contact Lens Wear*. The Dry Eye Institute, Lubock, Tex., 1986, incorporated herein by reference.

The most common treatment for dry eye involves temporary alleviation of the dry eye symptoms by topical application of a tear substitute that adds a volume of liquid to the anterior surface of the eye and related adnexa. Typical tear substitute compositions comprise water soluble, aqueous polymer compositions. Such compositions include, for example, saline solutions of polyvinyl alcohols, hydroxypropylmethyl cellulose or carboxymethyl celluloses. U.S. Pat. No. 4,421,748 teaches an artificial tear composition comprising an aqueous hypotonic solution of lecithin and a viscosity adjusting agent such as a solution soluble cellulose.

Methods used to quantify the effectiveness of tear substitutes for dry eye treatment solutions have not been standardized and many methods used in the art to quantify the results obtained with such tear substitute compositions are often inaccurate. For this reason, it is known that reported relief of dry eye symptoms using known tear substitutes varies considerably from subject to subject, and regardless of the method used to quantify relief using a tear substitute, relief often does not exceed several minutes.

The symptoms associated with dry eye are often exacerbated with subjects using contact lenses. In some cases, contact lens intolerance is caused in part or in total by the condition of dry eye and the symptoms thereof. For many subjects, contact lens intolerance is not overcome by topical application of tear substitutes. For these reasons, there is a need for improved compositions and processes for treatment of the dry eye condition.

An improved composition for dry eye treatment is disclosed and claimed in U.S. Pat. No. 4,914,088 granted Apr. 3, 1990 and incorporated herein by reference. This patent teaches the use of charged phospholipids and the treatment of dry eye symptoms which assist in replicating the tear film that would naturally occur in the eye. In accordance with the patent, the phospholipid composition, preferably in the form of an aqueous emulsion, is topically applied to the eye where it is believed to disperse over the ocular surface and form a film over the eye that replicates a lipid layer that would be formed by the spreading of a naturally occurring lipid secreted from the Meibomian glands over the surface of the eye during blinking. Because the phospholipid, when applied to the eye, carries a net charge, it is believed that the aligned molecules repel each other such that complex aggregate formation is prevented and the integrity of the phospholipid film is maintained. It is speculated in the patent that the film formed from the phospholipid helps in the formation of a barrier film reducing evaporation of the aqueous layer, thereby preserving the tear film.

SUMMARY OF THE INVENTION

The invention disclosed herein is an improvement over that disclosed in the above cited U.S. Pat. No. 4,914,088. In accordance with the invention disclosed herein, the dry eye treatment compositions are improved further whereby the longevity of an artificially formed tear film generated in an eye is significantly increased, its efficacy is significantly increased and variability from patient to patient is reduced.

The invention described herein is predicated on the discovery that an essentially non-polar oil is a desirable component of a dry eye treatment solution. The reason for using the non-polar oil may best be understood by an understanding of the mechanism by which a barrier capable of preventing dehydration is believed to be formed using the treatment composition of the invention. It is reported that a naturally occurring tear film comprises a complex coating with three separate layers. The inner layer in contact with the ocular surface of the eye is reported to be primarily composed of mucus and is believed to render the hydrophobic epithelial cell surface hydrophilic. The middle layer of the tear film is an aqueous layer. This layer is the thickest portion of the tear film and is a source of moisture for the eye and is further believed to function as an optical planarizing layer and to provide lubrication for the eye. The outer layer of the tear film, at its interface with the atmosphere and the eye, is an oily, naturally occurring lipid layer. This oily lipid layer is reported to act as a barrier that prevents evaporation of the aqueous layer, (Mishima and Maurice: The oily layer of the tear film and evaporation from the corneal surface, Exp. Eye Res. 1961; 1:39-45).

The polar lipid and non-polar oily lipid components of the tear film are believed to originate primarily from secretions of the Meibomian glands. The tear film is formed from these secretions and is constantly replenished over the aqueous layer of the tear film during blinking due to the eyelids spreading the lipid over the surface of the eye. By constantly spreading the polar and non-polar lipids over the eye during blinking, the tear film is maintained and evaporation of the aqueous middle layer of the tear film is believed to be minimized.

A cause of dry eye is believed to result from a deficiency in the lipid layer, the oily lipid layer or both. This deficiency may result from an inadequacy in the quantity of secretion from the Meibomian glands or an inadequacy in the quality of the secretion. Regardless of the cause of the deficiency, it is believed that the compromised lipid layer fails to act as an adequate barrier against evaporation of the aqueous portion of the tear film thus resulting in one form of the condition known as dry eye.

In accordance with the invention of U.S. Pat. No. 4,914,088, a charged phospholipid is added to the eye, preferably in the form of an aqueous emulsion. Upon contact of the phospholipid with the eye, it was speculated that the phospholipid dispersed over the ocular surface and formed a film over the eye that replicated the lipid layer that would normally be formed by the spreading of a naturally occurring lipid secreted from the Meibomian glands over the surface of the eye during blinking. Because the phospholipid, when applied to the eye, carried a net charge, most preferably a net negative charge, it was speculated that the aligned molecules repelled each other such that complex aggregate formation was prevented and the integrity of the phospholipid film maintained. It was believed that the film formed from the phospholipid layer acted as a barrier, reducing evaporation of the aqueous layer, thereby preserving the tear film.

In practice, it was found that treatment of dry eye symptoms with the phospholipid compositions claimed in U.S. Pat. No. 4,914,088 resulted in substantial improvement relative to treatment with prior art compositions. Films formed by the application of the phospholipid treatment composition to the eye were found to be long lasting and application of the treatment composition did not cause blurring of vision any more severe than the blurring resulting from the application of prior art compositions for dry eye treatment or even physiological saline.

Though the use of the dry eye treatment solutions of U.S. Pat. No. 4,914,088 provided relief of dry eye symptoms in the majority of patients treated as stated in said patent, more recently, with improved testing procedures, variance in efficacy from patient to patient was experienced and the variance was occasionally unpredictable. Further investigation revealed the reason for this variance and in accordance with the invention disclosed herein, has resulted in a treatment composition that is superior to the improved treatment composition of U.S. Pat. No. 4,914,088.

The treatment composition of the invention comprises a combination of a charged phospholipid and an essentially non-polar oil. Though the charged phospholipid and the non-polar oil can be separately applied to the eye, it is preferred that the two are combined in a single treatment composition, most preferably in the form of a finely divided aqueous oil in water emulsion having a dispersed phase with a particle size preferably not exceeding 50 microns, more preferably having a particle size less than 20 microns and most preferably having a particle size less than 5 microns. In use, the treatment composition of the invention disperses over the surface of the eye. A negatively charged phospholipid layer is believed to form an aligned film over the aqueous tear film with the charged ends of the phospholipid dissolved in the aqueous layer and the hydrophobic ends of the phospholipid, furthest removed from the aqueous layer, available to bond with the essentially non-polar oil layer thus causing the oil layer to disperse over the surface of the eye as a thin, contiguous and stable layer that acts as a barrier to evaporation. The phospholipid component of the thus formed tear film may be viewed as an intermediate bonding layer bonding the oil layer onto the surface of a relatively thick aqueous layer resulting in a film over the eye that provides mechanical lubrication to the eye and reduces evaporation of fluid from the surface of the eye. In addition, where a stable film is formed over the eye and maintained on the surface of the eye for a prolonged period of time, dissolution of a medicant in the treatment solution will result in an efficient system for delivering a medicament to the ocular surface over a prolonged period of time. Further, where the treatment composition contains a substantial quantity of water, the water added to the eye may augment the thickness of the aqueous portion of the tear film.

The above described behavior of the composition of the invention on the surface of an eye can be used to explain the somewhat unpredictable results obtained using the treatment compositions of U.S. Pat. No. 4,914,088. Recognizing that the tear film naturally occurring in the eye may be deficient in the phospholipid component, the oil component, or both, the treatment composition of said patent replenished only the phospholipid component of the deficient tear film. If the naturally occurring tear film was deficient only in the phospholipid component, but not in the oil component, the improvement realized by addition of the phospholipid component would be dramatic. If the naturally occurring tear film was deficient only in the oil component, an improvement occurred, but the improvement was not as dramatic. Finally, as in most cases, if the naturally occurring tear film was deficient in both the oily lipid and the polar lipid components, improvement was realized varying between moderate and significant dependent upon the extent of the deficiency of the oil component.

In U.S. Pat. No. 4,914,088, it was taught that certain neutral oils could be used in combination with the phospholipid composition. The neutral oils contemplated in the patent are polar oils such as triglycerides, cholesterol esters, natural waxes and cholesterol. The results obtained using combinations of charged phospholipids and neutral oils as described in said patent in some cases provided improvement over the use of the charged phospholipid alone. However, the polar neutral oils disclosed in the patent are not the essentially non-polar oils contemplated herein and the use of a non-polar oil in combination with the charged phospholipid as disclosed is an improvement over the use of a charged phospholipid in combination with a polar oil.

DESCRIPTION OF THE PREFERRED EMBODIMENTS

The treatment compositions of the invention are applied by topical application of a phospholipid having a net charge and an essentially non-polar oil to the eye. Topical application is by application of a treatment composition where preferably the two components are contained in a single liquid vehicle. The composition may be in the form of an emulsion, solution, salve, ointment, spray, etc. dependent upon the use of the treatment composition and the solubility properties of the materials used. Preferably, both the phospholipid and the non-polar oil are in the same solution and more preferably, are homogeneously distributed throughout a liquid vehicle, most preferably in the form of an aqueous oil in water emulsion where the non-polar oil comprises the dispersed (organic) phase of the emulsion.

Phospholipids suitable for purposes of the invention are known in the art to be complex and known to carry a net positive or negative charge under the conditions of use. The preferred materials are those carrying a net negative charge because the negatively charged material will be repelled by the negatively charged ocular surface thereby permitting the maintenance of a relatively thick aqueous layer. The positively charged phospholipid will be attracted to the negatively charged ocular surface thus compressing the tear film. Hence the positively charged phospholipids operate in a different manner than the negatively charged phospholipids and are lesser preferred.

It is known that complex phospholipids contain a polar group at one end of their molecular structure and a non-polar group at the opposite end of the molecular structure. A discussion of phospholipids can be found in Leninger, *Biochemistry*, 2 ed., Worth Publishers, New York, pp. 279-306, incorporate herein by reference.

Many complex phospholipids are known in the art. They differ in size, shape and the electric charge of their polar head groups. Phosphoglycerides are compounds where one primary hydroxyl group of glycerol is esterified to phosphoric acid, and the other two hydroxyl groups are esterified with fatty acids. The parent compound of the series is, therefore, the phosphoric acid ester of glycerol. This compound has an asymmetric carbon atom and, therefore, the term phosphoglycerides includes stereoisomers.

All phosphoglycerides have a negative charge at the phosphate group at pH 7, and the $pK_a$ of this group is in the range of 1 to 2. The head groups of phosphatidylinositol, phosphatidylglycerol including diphosphatidylglycerols (having the common name cardiolipins) and the phosphatidylsugars have no electric charge, and all are polar because of their high hydroxyl group content. Because of the negative charge of the phosphate group and the absence of a charge in the head group, the net charge of each of these materials is negative, and these materials are within the scope of the invention. Likewise, the head group of phosphatidylserine contains an alpha-amino group ($pK_a=10$) and, a carboxyl group ($pK_a=3$) and therefore, the molecule contains two negative charges and one positive charge at pH 7.0, giving it a net negative charge whereby this compound is also within the scope of the invention.

Complex phospholipids having a net positive charge are also within the scope of this invention but are lesser preferred for reasons given above and because of the high price and scarcity of these compounds. Examples of positively charged complex phospholipids within the scope of the invention are those containing the basic acyl amino acid groups. Such compounds are a subgroup within the family of the o-aminoacylphosphatidylglycerols.

In contrast to the charged phospholipids, the head groups of phosphatidylethanolamine and phosphatidylcholine (lecithin) have a positive charge at pH 7, and, thus, at this pH, these two phosphoglycerides are dipolar zwitterions with no net electric charge. Such compounds are not within the scope of this invention unless chemically reacted to impart a negative charge to the material.

Of the phospholipids discussed above, the net negatively charged phosphoglycerides are preferred for purposes of the invention. A more preferred class of phosphoglycerides are represented by the following generic formula:

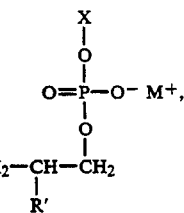

where R and R' are each fatty acid residues preferably having from 8 to 24 carbon atoms; X is hydrogen, a polyol or a 3'-O-aminoacylphosphatidylglycerol; and M is one equivalent of a countercation. R and R' are typically common natural fatty acids having an even or odd number of carbon atoms; they may be the same or may differ from each other; and they may be saturated, monounsaturated or polyunsaturated. Examples of fatty acid residues include laurate, myristate, palmitate, stearate, oleate, linoleate, octanoate, dodecate, lignocerate, etc.

Phospholipids are available from a variety of sources such as egg yolks, soy beans, etc. as is known in the art. These sources typically contain a mixture of components including natural lipids as exemplified by glycerides, cholesterol and cholesterol esters; phospholipids having a net charge of zero as exemplified by phosphatidylcholine, phosphatidylethanolamine; various unsaturated and saturated fatty acids; and charged phospholipids such as phosphatidylglycerol and phosphatidylinositol. The charged phospholipids are typically contained in these naturally occurring products in minor concentration, typically varying from below one percent up to 10 to 15 percent of the total composition.

A convenient, though lesser preferred source of the phospholipid in accordance with the invention starts with a phospholipid component from a natural source such as a plant i.e., soy bean; egg yolk or a synthesized equivalent thereof. The concentration of the charged phospholipid from such a natural source would likely be insufficient for purposes of treatment in accordance with the invention. Accordingly, a complex phospholipid having a net charge, preferably a net negative charge, would be added to such a phospholipid source to increase the total concentration of the complex charged phospholipids to a concentration required for treatment in accordance with the invention. Obviously, if a phospholipid from a natural source is negatively charged, a negatively charged phospholipid would be added to supplement the concentration of the same whereby the total net charge remains negative.

The most preferred phospholipid for purposes of this invention is a polyol with a net negative charge. The most preferred polyol phospholipids are the phosphatidylglycerols, including cardiolipins and phosphatidylinositols. Without wishing to be bound by theory, it is believed that the hydroxyl groups of the head groups of these phospholipids cause hydrogen bonding with the aqueous portion of the tear film thus stabilizing the film formed over the eye for an extended time.

The second component of the eye treatment composition is an essentially non-polar oil. As is known in the art, oils may be derived from animals, plants, nuts, petroleum, etc. Those derived from animals, plant seeds, and nuts are similar to fats and are primarily glycerides or fatty acids and consequently, contain a significant number of acid groups rendering the same polar and unsuitable for purposes of the invention. Alternatively, oils derived from petroleum are usually aliphatic or aromatic hydrocarbons that are essentially free of polar substitution and therefore suitable for purposes of the present invention provided the oil is refined so as to be compatible with human tissue such as the ocular surface. Preferably, the oil is a hydrocarbon oil having from 10 to 50 carbon atoms and more preferably, the oil is an saturated n-alkane or isoalkane having from 14 to 26 carbon atoms. Alkene hydrocarbons may be used but are less stable as the double bonds tend to oxidize. Aromatic oils are lesser preferred because it is known that aromatic compounds are for the most part unsuitable for application to the ocular surface.

The charged phospholipid and non-polar oil may be topically applied to the surface of the eye separately with the sequence of application preferably comprising first application of the phospholipid followed by the oil. One method of application could involve separately dispersing each of the phospholipid and the oil in a carrier liquid such as water to control concentration of the phospholipid or oil and topically applying each separately to the eye. Other methods of treatment comprise application of gels, creams, etc.

Preferably, the oil and the charged phospholipid are applied to the ocular surface as a combined treatment composition dispersed in a liquid carrier such as water. The most preferred treatment composition is a finely divided oil in water emulsion where the oil is the dispersed phase and the aqueous phase is the continuous phase of the emulsion.

One method of forming an emulsion of the charged phospholipid and the essentially non-polar oil is by agitating the phospholipid and oil in physiologic saline while warming the composition to a temperature in excess of the melting point of the phospholipid component. Agitation may be continued at an elevated temperature until a homogeneous dispersion is obtained. Agitation is preferably mechanical agitation. Emulsification by sonification may lead to the formation of unstable vesicles or liposomes and is undesirable. An emulsifying agent may be added to the formulation to stabilize the emulsion for long term storage, extend the shelf life, and thermal stability, though the phospholipid component does function as an emulsifying agent by itself.

The most preferred method for preparing a treatment solution in accordance with this invention comprises emulsifying the essentially non-polar oil and charged phospholipid using a microfluidizer and process as disclosed in U.S. Pat. No. 4,533,254 incorporated herein by reference. To form an emulsion using a microfluidizer, a premixed crude emulsion is pumped at high pressure into a unique fixed architecture interaction chamber, as disclosed in said patent, forming liquid jets or sheets. These jets or sheets then impinge upon each other in well fixed and defined micro channels within the chamber, resulting in a small zone of intense turbulence or cavitation which causes the dispersed phase to break into smaller droplets. In addition, the uniform application of this intense turbulence to each micro unit of fluid passing through the chamber yields a very narrow size distribution of the dispersed phase giving rise to more physically stable emulsions having particle sizes ranging from about 0.01 to 5.0 microns though emulsion having larger particles are suitable for purposes of the invention. Preferably, the dispersed oil phase of the emulsion has a particle size not exceeding 50 microns, more preferably not exceeding 25 microns and most preferably not exceeding 5.0 microns.

The concentration of the charged phospholipid in the treatment composition of the invention may vary within wide limits. A treatment composition containing the charged phospholipid in an amount as low as 0.01 weight percent of the total composition provides some benefit. A concentration of charged phospholipid varying between 0.1 to 7.0 percent of the total composition is a clinically practical concentration range for purposes of the invention. It should be noted that the most desired concentration for the charged phospholipid in the composition will vary from subject to subject though in general, the preferred concentration of the charged phospholipid varies between about 0.1 and 1.0 percent by weight of the total composition.

The essentially non-polar oil in the treatment composition may also vary within wide limits. A treatment composition containing the oil in a concentration of at least 0.1 percent by weight of the total composition provides some benefits. A preferred concentration range for the oil varies between about 0.2 and that concentration where an emulsion would be unstable or significant blurring might occur—i.e., 12.5 percent by weight of the total concentration or more and more preferably, between 0.5 and 5.0 percent by weight of the composition.

Other additives may be present in the treatment composition including those materials found in phospholipids derived from natural sources such as egg yolk and soy beans. Such materials include minor amounts of neutral lipids and oils such as one or more triglycerides, cholesterol esters, the natural waxes and cholesterol; high molecular weight isoprenoids; stabilizers, preservatives, pH adjusters to provide a composition preferably having a pH between about 5.0 and 8.5 and more preferably, between 6.0 and 7.4 and most preferably, between about 6.4 and 6.8; salt or sugar in sufficient concentration to form an isotonic or mildly hypotonic composition; etc., all as would be obvious to those skilled in the art. Medicaments are a particularly useful class of additives because the long term stability of the film formed over the surface of the eye using the compositions of the invention results in improved delivery of the medicament to the eye due to increased contact time of the medicament with the eye. Medicants suitable for delivery to the eye using the film forming compositions of the invention are those soluble in either the aqueous or oil phase of the composition. Illustrative medicaments are disclosed in published European Patent Application No 0 092 453 published Oct. 26, 1983, sections 5.3.1 and 5.3.2, incorporated herein by reference.

If the treatment composition is in the form of an emulsion, other additives are added to the treatment composition prior to formation of the emulsion using simple mixing techniques. The concentration of the additive is dependent upon the specific additive and preferably, total additive content in addition to the charged phospholipid and the non-polar oil are at a maximum concentration level whereby the total weight of the organics in the oil phase does not exceed 15 percent of the total weight of the emulsion.

The invention will be better understood by reference to the examples which follow where, in all examples, a tear film formed over an ocular surface was evaluated by shining a light source onto the ocular surface and projecting the reflection from the light source onto a video screen. The light source selected is one that illuminates a surface area on the ocular surface of approximately 10 $mm^2$. The reflection from the eye source reveals a series of colored waves of varying color. The color of the waves are correlated with a protocol of known film thickness. In this way, tear film can be evaluated over a period of real time and rated in accordance with the following scale:

| Rating | Film Characteristics | Film Quality |
|---|---|---|
| A | Colored waves - all colors including greens and blues. Waves extend half between lower lid and inferior pupillary edge. Film thickness in excess of 170 nm. | Excellent |
| B to C | Colored waves of yellow, brown and red. Film thickness ranging between 90 and 170 nm. | Good |
| D | Waves visible but of no constant color other than possible intermittent yellow coloration. Film thickness of about 90 nm. | Fair |
| F | No waves and no color. This film of a thickness less than 90 nm. | Poor |

In the examples, the designation (+) or (−) following a letter means a minor deviation from the standard given. In all examples, the eye was evaluated and rated before application of an eye treatment formulation and following application of the formulation. In the latter case, the evaluation occurred after formation of a film of the added treatment formulation.

EXAMPLE 1

This example compares the use of several dry eye treatment formulations comprising (A) a phospholipid without an oil, (B) a phospholipid in combination with a non-polar oil (preferred embodiment), C) a phospholipid in combination with a polar oil, and (D) a phospholipid in combination with another non-polar oil; using a variety of subjects with eyes having tear films of varying quality (prior to treatment) from poor to good. The test method described above was used for purposes of evaluation. The test solutions were in the form of emulsions formed using the methods of U.S. Pat. No. 4,914,088.

The following formulations were used:

| Component | Amount (% by Wt) |
|---|---|
| Formulation A | |
| Phosphatidyl Choline[1] | 0.085 |
| Phosphatidyl Glycerol | 0.085 |
| Sorbic acid | 0.100 |
| Ethylene diamine tetra acetic acid | 0.100 |
| Water | to 1 liter |
| Formulation B | |
| Phosphatidyl Choline[1] | 0.085 |
| Phosphatidyl Glycerol | 0.085 |
| Sorbic acid | 0.100 |
| Ethylene diamine tetra acetic acid | 0.100 |
| glycerol | 2.000 |
| Alkane Oil[2] | 1.00 |
| Water | to 1 liter |
| Formulation C | |
| Phosphatidyl Choline[1] | 0.085 |
| Phosphatidyl Glycerol | 0.085 |
| Ethylene diamine tetra acetic acid | 0.100 |
| Sorbic acid | 0.100 |
| Oleic acid palmityl ester | 0.300 |
| Water | to 1 liter |
| Formulation D | |
| Phosphatidyl Choline[1] | 0.085 |
| Phosphatidyl Glycerol | 0.085 |
| Ethylene diamine tetra acetic acid | 0.100 |
| Sorbic acid | 0.100 |
| Myristic acid ethyl ester | 0.300 |
| Water | to 1 liter |

[1] The phosphatidyl choline used was a pure synthesized material.
[2] Mineral oil sold under the trade name Drakeol 21 and available from Penreco Corp. of Butler, PA.

The eye treatment formulations were applied to the eye by dipping a glass rod in the treatment formulation and applying a drop of the treatment formulation to the eye from the glass rod.

The following results were obtained:

| Patient Number | Treatment Formulation | Rating Before Treatment | Rating After Treatment |
|---|---|---|---|
| 1 | A | F+ | D |
| 2 | A | F | C− |
| 3 | A | D | C− |
| 4 | A | C | B |
| 5 | A | C | C+ |
| 6 | A | C | C |
| 7 | A | C | C |
| 8 | A | C− | C |
| 9 | A | B | B |
| 10 | A | A | A |
| 11 | A | A | A+ |
| 12 | B | F | D+ |
| 13 | B | F | D |
| 14 | B | D+ | B |
| 15 | B | D | C− |
| 16 | B | C | B− |
| 17 | B | C | B |
| 18 | B | C | C |
| 19 | B | C | C+ |
| 20 | B | C | A− |
| 21 | B | B | B+ |
| 22 | B | A | A |
| 23 | B | A | A+ |
| 24 | C | F+ | C |
| 25 | C | D− | C− |
| 26 | C | D | B+ |
| 27 | C | C− | B |
| 28 | C | C | B− |
| 29 | C | C | B+ |
| 30 | C | B | B |
| 31 | C | B | B− |
| 32 | C | B− | B− |
| 33 | C | A+ | A |
| 34 | C | A− | A− |
| 35 | C | A | A |
| 36 | D | F | D |
| 37 | D | D | C |
| 38 | D | D | B− |
| 39 | D | C | C+ |
| 40 | D | C− | B− |
| 41 | D | C | B+ |
| 42 | D | C | C |
| 43 | D | C− | B− |

-continued

| Patient Number | Treatment Formulation | Rating Before Treatment | Rating After Treatment |
|---|---|---|---|
| 44 | D | B+ | B+ |
| 45 | D | B | B |
| 46 | D | A+ | A |
| 47 | D | A− | A− |
| 48 | D | A | A |

From the above data, it can be seen that treatment with a charged phospholipid without the presence of the oil improved the tear film in most cases, but the improvements were not dramatic. By comparison, combination of the phospholipid with the non-polar oil improved the tear film in practically all cases and in some cases, the improvement was significant. The results obtained using the combination of the charged phospholipid with an oil containing some polar groups showed improvement in some cases, but the improvement was not dramatic. In all cases, it should be noted that the phospholipid concentration in the treatment formulation was relatively low and higher concentrations of the phospholipid would be expected to provide greater improvements.

EXAMPLE 2

This example compares the use of several dry eye treatment formulations comprising (A) a phospholipid without an oil, (B) a phospholipid in combination with a non-polar oil (most preferred embodiment), (C) a polar oil alone, and (D) a non-polar oil alone; using a variety of subjects with eyes having tear films of varying quality (prior to treatment) from poor to good. The test method described above was used for purposes of evaluation. Test solutions A and B were in the form of emulsions formed using the methods of U.S. Pat. No. 4,533,254 thereby producing an emulsion with a very finely dispersed oil phase. Solutions C and D were applied as "neat" oils using a glass rod immersed in the oil which is wiped to provide a thin oil layer and then touched to the inner lining of the lower lid of the eye to dispense the oil onto the eye.

The following formulations were used:

| Component | Amount (% by Wt) |
|---|---|
| Formulation A | |
| Phosphatidyl Choline[1] | 0.05 |
| Phosphatidyl Glycerol | 0.05 |
| Sorbic acid | 0.10 |
| Ethylene diamine tetra acetic acid | 0.10 |
| Water | to 1 liter |
| Formulation B | |
| Phosphatidyl Choline[1] | 0.05 |
| Phosphatidyl Glycerol | 0.05 |
| Sorbic acid | 0.10 |
| Ethylene diamine tetra acetic acid | 0.10 |
| Alkane Oil[2] | 1.00 |
| Water | to 1 liter |

[1] The phosphatidyl choline used was a pure synthesized material.
[2] Mineral oil sold under the trade name Drakeol 21 and available from Penreco Corp. of Butler, PA.

Treatment Formulations A and B were made and applied to the eye using the procedures of Example 1. Formulations C and D were neat solutions of safflower oil (a polar oil) and the mineral oil (non-polar oil) used for preparation of Formulation B, respectively.

The following results were obtained:

| Patient Number | Treatment Formulation | Rating Before Treatment | Rating After Treatment |
|---|---|---|---|
| 1 | A | F | D |
| 2 | A | F | A− |
| 3 | A | F | D |
| 4 | A | F | C |
| 5 | A | F | B |
| 6 | A | F | A |
| 7 | A | F | F |
| 8 | A | F | A+ |
| 9 | A | F | B+ |
| 10 | A | F | B |
| 11 | A | F | D |
| 12 | A | D | A |
| 13 | A | D+ | B− |
| 14 | A | B | A |
| 15 | A | B− | B |
| 16 | A | B− | A |
| 17 | A | A− | A |
| 18 | B | F | A |
| 19 | B | F | A |
| 20 | B | D | A+ |
| 21 | B | D | C+ |
| 22 | B | C | A |
| 23 | B | A | A |
| 24 | C | F | Vision blurred |
| 25 | C | D | F |
| 26 | C | C | D |
| 27 | C | B | C |
| 28 | C | A | F− |
| 29 | C | A | F |
| 30 | C | A | F |
| 31 | D | F | A |
| 32 | D | F | C |
| 33 | D | D | A+ |
| 34 | D | F | A+ |
| 35 | D | F | A |
| 36 | D | B | A+ |
| 37 | D | B | A+ |
| 38 | D | A | A |
| 39 | D | A | A |

In this example, the use of a charged phospholipid improved results in all cases though the results varied significantly from patient to patient. As in Example 1, the concentration of the phospholipid was relatively low and greater improvement would be expected with higher concentrations of the phospholipid. Variation in the results obtained is believed to be due to the presence of some natural oils in the eye with the charged phospholipid assisting in the formation of a controlled oil film over the eye. The combination of the charged phospholipid with the non-polar oil provided dramatic improvement. The results of this example should be compared to the results obtained for Example 1 using the same formulation where the differences were in the degree of dispersion of the emulsion. This establishes that a fine particle size promotes the formation of a film. The use of a polar oil alone for dry eye treatment resulted in an excessively thick film over the eye with substantial blurring. Use of a non-polar oil in accordance with the invention provided a superior film in most cases but vision was blurred, probably as a consequence of failure to fully disperse the film over the eye and possibly due to the application of an excessive quantity of oil as a result of the method of administering the oil to the eye.

We claim:

1. An artificial tear film over the aqueous layer of an eye comprising a layer of a complex phospholipid having a net charge over said aqueous layer and a layer of an essentially non-polar oil over said phospholipid layer, said complex phospholipid and oil layers being present in an amount sufficient to form a tear film over the ocular surface and below that amount that would result in significant prolonged blurring of vision.

2. The tear film of claim 1 where the phospholipid carries a net negative charge.

3. The tear film of claim 1 where the phospholipid is phosphatidylglycerol.

4. The tear film of claim 2 where the oil is a liquid hydrocarbon oil.

5. The tear film of claim 1 where the oil is an n-alkane oil.

6. The tear film of claim 5 where the n-alkane oil is mineral oil.

7. The tear film of claim 5 where the n-alkane oil has from 10 to 50 carbon atoms.

8. The tear film of claim 7 where the n-alkane oil has from 14 to 26 carbon atoms.

9. The tear film of claim 2 containing a material for medicating the eye.

10. The tear film of claim 2 overcoated with a contact lens.

11. A method for reducing evaporation from an aqueous tear film over the surface of an eye, said method comprising applying an admixture of a complex phospholipid having a net charge and a non-polar oil over said tear film, said complex phospholipid and said non-polar oil in said admixture being added to the eye in an amount sufficient to form a tear film over the ocular surface below that amount that would cause significant blurring of vision when dispersed over the eye as a film.

12. The method of claim 11 where the phospholipid carries a net negative charge.

13. The method of claim 11 where the phospholipid is phosphatidylglycerol.

14. The method of claim 12 where the oil is a liquid hydrocarbon oil.

15. The method of claim 14 where the oil is an n-alkane oil having from 10 to 50 carbon atoms.

16. The method of claim 15 where the n-alkane oil has from 14 to 26 carbon atoms.

17. The method of claim 15 where the oil is mineral oil.

18. The method of claim 12 where the admixture is applied to the eye in the form of an emulsion.

19. The method of claim 18 where the emulsion is an oil in water emulsion where the oil phase is dispersed in the aqueous phase.

20. The method of claim 19 where the phospholipid component and the essentially non-polar oil are each present in the emulsion in a concentration of at least 0.01 percent by weight.

21. The method of claim 20 where the phospholipid component is present in the emulsion in a concentration ranging between 0.1 and 7.0 percent by weight and the oil is present in an amount ranging between 0.2 and 12.5 percent by weight.

22. The method of claim 20 where the phospholipid component is present in the emulsion in a concentration ranging between 0.1 and 1.0 percent by weight and the oil is present in an amount ranging between 0.5 and 5.0 percent by weight.

23. The method of claim 20 where the admixture of the phospholipid and the oil contains a medicament.

24. A method for reducing evaporation of an aqueous tear film over the surface of an eye, said method comprising applying an essentially non-polar oil over a film of a charged phospholipid overlying said tear film, said non-polar oil being added in an amount sufficient to form a tear film over the ocular surface and below that amount that would cause significant blurring of vision when dispersed over the eye as a film.

25. The method of claim 24 where the phospholipid is present as a consequence of glandular secretion.

26. The method of claim 24 where the phospholipid is added to the eye before the oil and carries a net negative charge.

27. The method of claim 24 where the oil is a hydrocarbon oil.

28. The method of claim 27 where the hydrocarbon oil is an n-alkane oil having from 10 to 50 carbon atoms.

29. The method of claim 28 where the n-alkane oil has from 14 to 26 carbon atoms.

30. The method of claim 27 where the oil is mineral oil.

31. A treatment composition for topical application over the eye, said composition comprising an emulsion of an essentially non-polar oil and a charged phospholipid in an aqueous carrier, said emulsion being an oil in water emulsion, said emulsion containing said complex phospholipid and said non-polar oil in an amount sufficient to form a tear film over the ocular surface and below that amount that would cause significant blurring of vision when dispersed over the eye as a film when about 1 drop of said emulsion is added to the eye.

32. The composition of claim 31 where the phospholipid carries a net negative charge.

33. The composition of claim 31 whereas the phospholipid is phosphatidylglycerol.

34. The composition of claim 32 where the oil is a hydrocarbon oil.

35. The composition of claim 34 where the oil is an n-alkane oil having from 10 to 50 carbon atoms.

36. The composition of claim 35 where the n-alkane oil has from 14 to 26 carbon atoms.

37. The composition of claim 34 where the oil is mineral oil.

38. The composition of claim 30 where the phospholipid component and the essentially non-polar oil are each present in the emulsion in a concentration of at least 0.01 percent by weight.

39. The composition of claim 38 where the phospholipid component is present in the emulsion in a concentration ranging between 0.1 and 1.0 percent by weight and the oil is present in an amount ranging between 0.5 and 5.0 percent by weight.

40. The composition of claim 30 containing a material for medicating the eye.

41. The tear film of claim 1 where the film contains a natural wax.

42. The method of claim 11 where the admixture contains a natural wax.

43. The method of claim 19 where the dispersed oil phase further contains a natural wax.

44. The treatment composition of claim 24 where said composition further contains a natural wax.

45. The method of claim 31 where the mixture further contains a natural wax.

* * * * *